United States Patent
Krumme et al.

(10) Patent No.: US 8,242,639 B2
(45) Date of Patent: Aug. 14, 2012

(54) INDUCTIVE ROTARY JOINT WITH LOW LOSS SUPPLY LINES

(75) Inventors: Nils Krumme, Feldafing (DE); Michael Tekloth, München (DE); Michael Bley, Maisach (DE); Arno Zimpfer, Mammendorf (DE)

(73) Assignee: Schleifring und Apparatebau GmbH, Fürstenfeldbruck (DE)

( * ) Notice: Subject to any disclaimer, the term of this patent is extended or adjusted under 35 U.S.C. 154(b) by 283 days.

(21) Appl. No.: 12/575,986

(22) Filed: Oct. 8, 2009

(65) Prior Publication Data

US 2010/0090536 A1 Apr. 15, 2010

(30) Foreign Application Priority Data

Oct. 9, 2008 (DE) .......................... 10 2008 042 700

(51) Int. Cl.
*H01F 27/42* (2006.01)
(52) U.S. Cl. ................ 307/104; 333/25; 333/26; 378/4; 378/19; 378/196; 378/197; 378/198
(58) Field of Classification Search .................. 307/104; 378/101, 15
See application file for complete search history.

(56) References Cited

U.S. PATENT DOCUMENTS

| 3,458,239 | A | * | 7/1969 | Dorsman | 310/90.5 |
| 5,159,697 | A | * | 10/1992 | Wirth | 378/93 |
| 6,798,309 | B2 | | 9/2004 | Lohr et al. | |
| 7,054,411 | B2 | | 5/2006 | Katcha et al. | |
| 7,397,896 | B2 | * | 7/2008 | Beyerlein | 378/107 |
| 7,634,046 | B2 | * | 12/2009 | Krumme | 378/19 |
| 2009/0060123 | A1 | * | 3/2009 | Nakayama et al. | 378/15 |
| 2009/0284323 | A1 | * | 11/2009 | London | 333/25 |
| 2010/0066340 | A1 | * | 3/2010 | Delforge | 323/305 |

FOREIGN PATENT DOCUMENTS

DE 10356109 7/2005

* cited by examiner

*Primary Examiner* — Rexford Barnie
*Assistant Examiner* — Toan Vu
(74) *Attorney, Agent, or Firm* — Meyertons, Hood, Kivlin, Kowert & Goetzel, P.C.; Eric B. Meyertons

(57) ABSTRACT

An inductive rotary joint for computer tomographs includes an inverter and an inductive rotary coupler. A primary winding of the inductive rotary coupler is fed by the inverter via a line, with energy transmitted by the inductive rotary coupler being supplied to a load through a secondary winding. The line includes at least two coaxial lines, each coaxial line having an outer conductor or shield with the two outer conductors or shields being interconnected along a major part of their length, and an inner conductor, with the inner conductors being supplied by the inverter with voltages, the sum of which is substantially equal to zero.

26 Claims, 3 Drawing Sheets

INDUCTIVE ROTARY JOINT WITH LOW LOSS SUPPLY LINES

PRIORITY CLAIM

This application claims priority from pending German Application No. 10 2008 042 700.4 filed on Oct. 9, 2008

BACKGROUND OF THE INVENTION

1. Field of the Invention

The invention relates to an inductive non-contacting rotary joint particularly for computer tomographs, and also to a line arrangement for transmitting electrical energy from an inverter to a stationary coupler of the inductive rotary joint.

2. Description of the Relevant Art

A non-contacting inductive rotary joint for transmission of power in a computer tomograph is disclosed in U.S. Pat. No. 7,054,411 B2. An a.c. voltage in a range of typically 10 kHz to 100 Mhz is generated with a power inverter. This is fed into the primary winding of an inductive non-contacting rotary joint. This primary winding is connected to the stationary part of the gantry of the computer tomograph. Disposed to be movable relative to this is the secondary winding on the rotatable part of the gantry. It is magnetically coupled to the primary winding. The a.c. voltage transmitted to the secondary winding is rectified by means of a rectifier block and smoothed with capacitors connected to follow. This d.c. voltage then can be applied to effect supply to various electronic components. Furthermore, energy for feeding the X-ray tube is coupled out via a second secondary winding. For this, the a.c. voltage of the secondary winding of the rotary joint is fed into a high voltage transformer on the output side of which a cascade for generating a high voltage of an order of magnitude of 100 kV is disposed. This high voltage is used to supply the X-ray tube.

The amounts of power to be transmitted here are within a range of 10 kW to far beyond 100 kW. The power inverter for generating an a.c. voltage in this power class is usually installed in a location away from the gantry of the computer tomograph. Thus, the gantry in which a patient is examined can be designed to be as small and elegant as possible. In addition, cooling of the gantry is simplified because here it is not necessary also to lead away the power loss of the inverter. Problems are caused by the electrical connection between the inverter and the primary side of the inductive power transmitter. Thus, here the energy needed must be transmitted as a medium frequency signal via a cable having a length of several meters. In conventional cables high losses occur along the line, which on the one hand leads to a distinct reduction of the efficiency of the entire arrangement, and on the other hand to heating of the cable to an extent that it also needs to be cooled.

SUMMARY OF THE INVENTION

The embodiments are based on the object of redesigning a computer tomograph having a rotary joint, redesigning a rotary joint, and also redesigning a cable connection between a power inverter and an inductive rotary joint, in such manner that even with high transmitted amounts of power of a magnitude of 100 kW the losses in a conductor system remain small, so that it needs no additional cooling.

In an embodiment these object are achieved with an inductive rotary joint, including an inverter and an inductive rotary coupler having a primary winding and a secondary winding, in which the primary winding of the inductive rotary coupler is fed by the inverter via a first line, and energy transmitted by the inductive rotary coupler is delivered to a load from a secondary winding via a second line; wherein at least one of the first and second lines include at least two coaxial lines, each having an outer conductor and an inner conductor; the outer conductors are interconnected in an electrically conductive manner along a major part of their length; and each of the inner conductors is supplied by the inverter with voltages, with a sum of the voltages supplied to the inner conductors being substantially equal to zero.

In an embodiment these objects are also achieved with an Inductive rotary joint, including an inverter and an inductive rotary coupler having a primary winding and a secondary winding, in which the primary winding of the inductive rotary coupler is fed by the inverter via a first line, and energy transmitted by the inductive rotary coupler is delivered to a load from a secondary winding via a second line; wherein at least one of the lines includes at least one coaxial line having an inner conductor and an outer conductor; and a sum of currents flowing through the inner conductor and the outer conductor is substantially equal to zero.

In an embodiment the above objects are also achieved with a line arrangement for coupling-on a load to an inverter, including at least two coaxial lines, each having an outer conductor and an inner conductor; wherein the outer conductors of the at least two coaxial lines are interconnected in an electrically conductive manner along a major portion of their length; and each of the inner conductors is supplied with voltages, with a total sum of the voltages supplied to the inner conductors being substantially equal to zero.

In an embodiment the above objects are also achieved with a computer tomograph including an inductive rotary joint of the kinds described above, or including a line arrangement as described above.

BRIEF DESCRIPTION OF THE DRAWINGS

In the following the invention will be described by way of example, without limitation of the general inventive concept, on examples of embodiment and with reference to the drawings.

Figure 1:
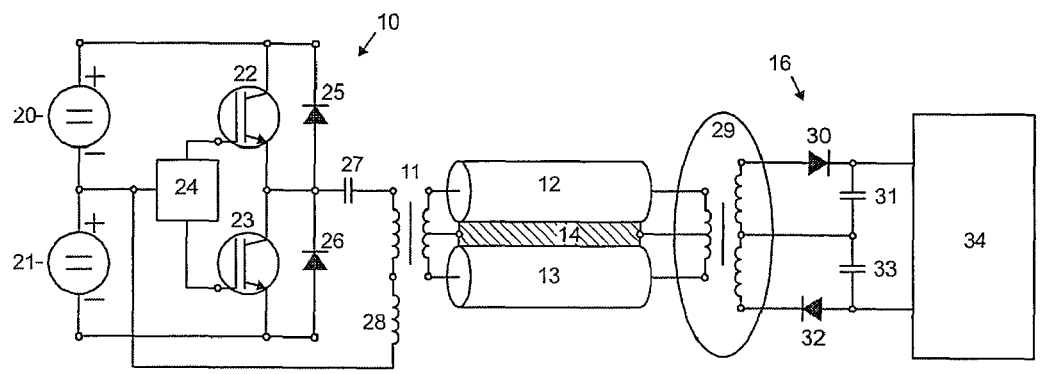
FIG. 1 schematically shows in a general form an inverter circuit coupled to a load.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

FIG. 1 shows an arrangement, having an example of an inverter circuit in the form of a half-bridge circuit, and also a specific embodiment of a load.

The inverter circuit 10 includes two voltage sources 20 and 21 which generate a balanced supply voltage. Two power switches 22 and 23, here shown by way of example as IGBTs, switch an output alternately to a positive voltage of a first voltage source 20 or to a negative voltage of a second voltage source 21. Control of the power switches is effected by a control unit 24. Recovery diodes 25 and 26 are provided for protection of the IGBTs and for receiving an inverse current. A load of the inverter is supplemented by a series capacity 27 and also by a series inductance 28 together with remaining components to form a series resonance circuit operating at a given series resonance frequency. This series resonance circuit is connected to a reference point between both voltage sources. The control of the power switches by means of the control unit 24 is effected so that the circuit operates preferably at the series resonance frequency or close to the series resonance frequency. For electrical separation of the load circuit from the inverter, and also for generation of a balanced bipolar output voltage, an isolation transformer 11 is provided. This generates at both ends of its winding an output voltage which is balanced with reference to a center tap of the winding. A signal from the isolation transformer 11 is now applied via a line to the primary winding of a rotary joint 29. Here the line consists of a first coaxial line 12 and a second coaxial line 13. Outer conductors or shields of the two lines are interconnected via a connection 14 along the length of both lines. At the same time the shield ends proximate to the isolation transformer are connected to the center tap thereof, and the shield ends proximate to the rotary joint 29 are connected to the center tap of its primary winding.

By way of example a secondary winding with a center tap is illustrated on the secondary side of the rotary joint 29. For connecting this secondary winding to further components, a line arrangement (not illustrated here) also can be used. The secondary winding supplies a d.c. voltage signal to the load 34 via two rectifier diodes 30 and 32 and also smoothing capacitors 31 and 33. This load can be any desired electronic component group on a rotating part of the computer tomograph, or also a high voltage generator for feeding an X-ray tube.

Figure 2:
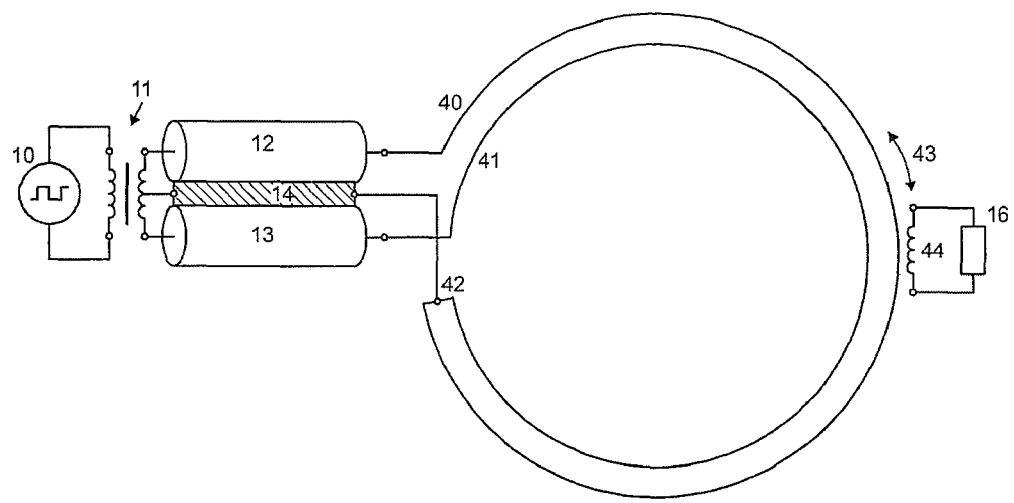
FIG. 2 schematically shows a detailed illustration of a rotary joint.

FIG. 2 schematically discloses an embodiment with a detailed illustration of a rotary joint.

The inverter 10 simply illustrated here feeds, again via the isolation transformer 11, the line consisting of the first coaxial line 12 and also the second coaxial line 13, which both have their shields interconnected via the connection 14. The signal at the output of the line is fed into the two coupling conductors 40 and 41. Both coupling conductors have their ends joined together to form an end point 42 which in turn is connected to the outer conductors or shields of the two coaxial lines 12 and 13. The current flowing through the coupling conductors generates a magnetic field which is picked-up by a coupling-out coil that is movable along a rotation direction 43, and a current is relayed to the load 16.

Figure 3:
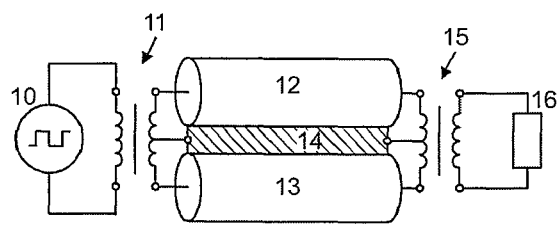
FIG. 3 shows another embodiment of an inverter circuit coupled to a load.

FIG. 3 shows a greatly simplified embodiment.

An inverter 10 feeds, via the isolation transformer 11 which in particular generates a balanced output signal, a line having a first coaxial conductor 12 and a second coaxial conductor 13, the outer conductors or shields of which are interconnected along their entire length via the connection 14. Coupled to the output end of the line is an output transformer 15 which can be a rotary joint, for example.

Figure 4:
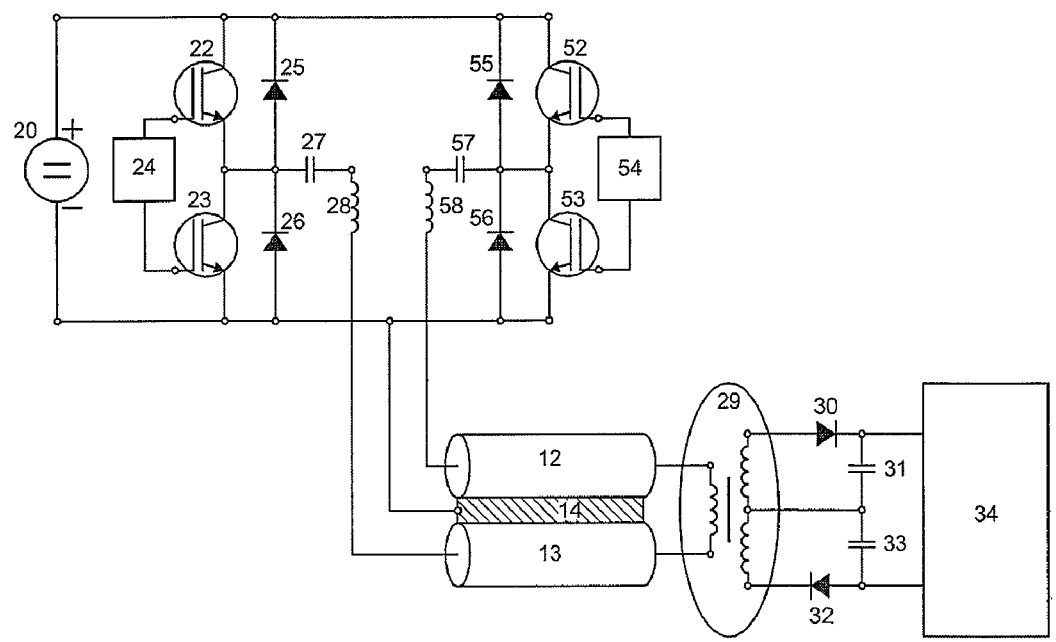
FIG. 4 shows a circuit variant having a full bridge circuit.

FIG. 4 discloses a circuit variant having a full bridge circuit (H-bridge circuit). This full bridge circuit includes most of the components of the previously described half-bridge circuit, and also a second set of IGBTs 52, 53 with recovery diodes 55, 56 and a control circuit 54. Here the control voltage is implemented only with a first voltage source 20. Two series capacities 27 and 57 and also two series inductances 28 and 58 are located in an output region. These have been included in the drawing by way of example for reasons of symmetry. Of course, in each case only one series inductance or series capacity could be used. As an alternative to each series inductance mentioned in this document, basically also a stray inductance of a transformer, in particular a rotary joint, could be used. The series inductances 28 and 58 also can take the form of a current-compensated choke. As distinct from the previously described half-bridge circuit, here the shield connection 14 of the line is connected to the negative current path from the negative output of the voltage source 20. This potential has been chosen here as an arbitrary reference potential. In the same way a connection to the positive current path also would be possible. Because here the outer conductors or shields are at a potential which is not symmetrical with respect to the output voltage, the center tap of the rotary joint 29 consequently has not been connected to the connection 14 between outer conductors or shields. However, a connection of this kind is possible. Because of the two series capacities 27 and 57, the load circuit is electrically separated from the inverter. Therefore the potential of the shields also can be chosen freely.

Figure 5:
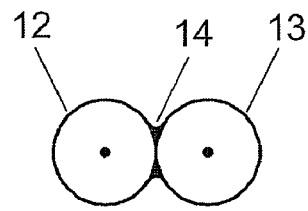
FIG. 5 shows a cross-section through a line having two conductors.

FIG. 5 shows a cross-section of a line having two coaxial lines. Here the two coaxial lines 12 and 13 are shown in cross-section together with their inner conductors illustrated at the centers. The connection 14 is here effected, for example, as a soldered connection between the outer conductors.

Figure 6:
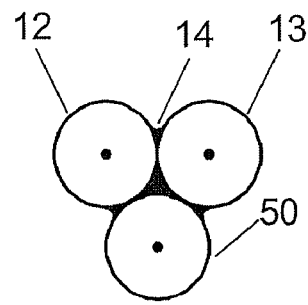
FIG. 6 shows a cross-section through a line having three conductors.

FIG. 6 shows an embodiment with three coaxial lines in cross-section. Based on FIG. 5, here an additional third coaxial line 50 is disposed and electrically connected with the two other coaxial lines along its entire length. Basically the number of conductors is not limited. Thus, lines can be implemented having also a larger number of conductors.

Figure 7:
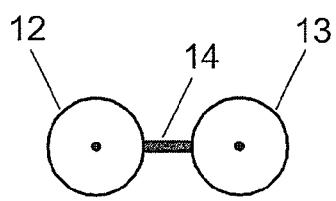
FIG. 7 shows another embodiment of a balanced double line.

FIG. 7 shows another embodiment of a balanced double line. Here the two coaxial lines 12 and 13 are interconnected via a connection 14 in the form of a web.

Figure 8:
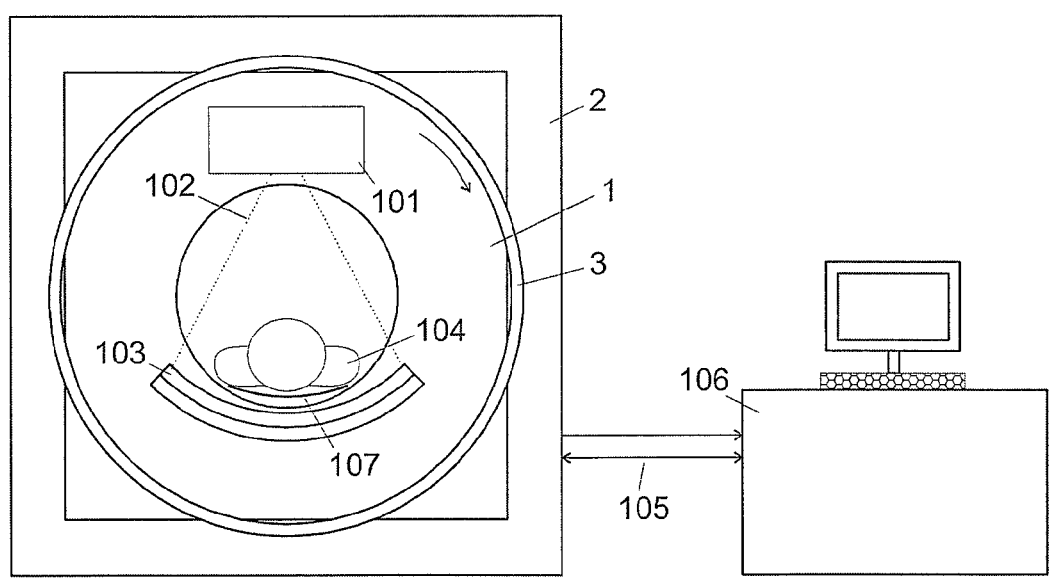
FIG. 8 shows a computer tomograph.

FIG. 8 shows a computer tomograph. The computer tomograph (CT scanner) includes two main mechanical parts. A stationary part 2 serves as a base and support for the entire instrument, in which the rotating part revolves. The patient 104 is positioned on a berth 107 in the opening of the rotating part. An X-ray tube 101 and also a detector 103 disposed opposite thereto are provided for scanning the patient by means of X-rays 102. The X-ray tube 101 and the detector 103 are disposed on the rotating part 1 to be rotatable. A rotary joint 3 serves for electrical connection between the rotating part 1 and the stationary part 2. With this, on the one hand the high electrical power for feeding the X-ray tube 101 is transmitted in the direction of the rotating part 1, and simultaneously the raw data of the image are transmitted in the opposite direction. Parallel to this, communication of control information in both directions is provided. An evaluation and control unit 106 serves for operation of the computer tomograph, and also for displaying the generated images. Communication with the computer tomograph is effected via a bidirectional link 105.

The inductive rotary joint, particularly for computer tomographs, includes an inverter 10 and an inductive rotary coupler 29. The inverter 10 transforms a rectified input voltage of a supply network to a medium frequency voltage having a typical frequency range of 10 kHz to 100 kHz. It consists typically of a full bridge or also a half-bridge circuit, preferably built-up with IGBTs. For suppression of high-frequency interference, the inverter also can include filter elements, for example inductances 28 or capacities 27. Furthermore, advantageously at least one series capacity 27 is dimensioned so that it compensates the stray inductance of the rotary coupler 29 at a given resonance frequency. The inverter is then operated preferably directly at, or close to, this resonance frequency, so that the impedance consisting of series capacitor and stray inductance of the rotary coupler is minimal. The output voltage of the inverter is transmitted to the primary winding of the inductive rotary coupler via a first line. This primary winding is typically disposed to be stationary. Rotatable relative to this, and magnetically coupled with this is a secondary winding which is connected in an electrically conductive manner to a load 16 via a second line. Advantageously, the output signal of the secondary winding is rectified and filtered via a rectifier and filter capacitors. A voltage converter or inverter connected to follow then converts the voltage to various voltages for various electronic components on the rotating part of the computer tomograph. Alternatively or additionally, the a.c. voltage at the output of the secondary winding can be supplied to a further transformer, such as for example a high voltage transformer.

In an embodiment, the transmission line includes at least two coaxial lines 12, 13 having outer conductors, here also referred to as shields, which are electrically connected to each other along the major part of their lengths. The inner conductors of the coaxial lines are supplied with voltages, the sum of which is substantially equal to zero. Each of these coaxial lines 12, 13 has a certain capacity inside the line itself between the inner and the outer conductor. Because the voltages have a zero sum, the capacitive currents of the entire line arrangement at every point along the line also have the value zero, when they can flow together at every point of the line. For the sake of clarity of illustration, let the line be disposed with its longitudinal axis along an X-axis. The concept of a point of a line is related to the length of the line, i.e. to a point on the X-axis. The embodiments also result in smallest of losses through capacitive currents which in conventional lines would flow along the entire length of a line. Furthermore, owing to the interconnection of the outer conductors or shields of the lines, eddy currents in each section along the length of the line can compensate each other at least partially, so that also the losses owing to magnetic fields in the line system compensate each other.

In another embodiment, the line includes exactly two coaxial lines 12, 13. The inner conductors of these two coaxial lines are fed with equally high voltages of opposite polarities. Thereby the above described effect can be achieved.

In another embodiment, the inverter 10 has a three-phase bridge circuit which generates a three-phase alternating signal. With this signal the sum of the voltages is approximately equal to 0 V. A three-phase inverter can be fabricated particularly economically. Here, in particular, the electrical load is distributed among three power-switch stages which accordingly can be dimensioned to be smaller than one single stage.

In another embodiment, the inverter 10 has a full-bridge circuit and generates a balanced alternating signal.

In another alternative embodiment, the inverter 10 has a half-bridge circuit. Now in order to generate a balanced alternating signal, a transformer 11 is connected in between the inverter 10 and the line.

In another embodiment, an isolation transformer 11 is connected in between the inverter 10 and the line. This isolation transformer 11 can admit of shifts of potential between the gantry of the computer tomograph together with the rotary joint 29, and the inverter circuit 10, and also can interrupt parasitic currents.

It is of especial advantage when the outer conductors of the at least two coaxial lines 12, 13 are connected to each other in an electrically conducting manner along their entire length. Thereby the desired effect can be achieved in a particularly efficient manner.

Furthermore, it is of special advantage when the outer conductors of the at least two coaxial lines are connected to each other via large-surface-area contact. Then contact resistances are lowest, and the compensation of magnetic fields is at its best, Thereby a minimization of losses can be achieved.

In another embodiment, the outer conductors of the at least two coaxial lines 12 and 13 are connected to each other by a multitude of electrical connections. These connections can be, for example, soldering joints or also short connecting leads. An embodiment of this kind is sometimes necessary for reasons of fabrication when, for example, a soldered connection along the entire length of a coaxial line is not possible.

Furthermore, it is of advantage when the outer conductors of the at least two coaxial lines are connected to a circuit ground, or a grounded conductor. Therewith, on the one hand, any flowing compensating currents can be passed to ground and, on the other hand, in the case of a grounded conductor a protective grounding also can be achieved.

An embodiment includes a line arrangement for coupling-on a load 16 to an inverter 10. The line arrangement includes the at least two coaxial lines 12, 13, the outer conductors of which are connected to each other along the major part of their lengths. Furthermore, the inner conductors are supplied with voltages, the total sum of which is substantially equal to zero.

Another embodiment relates to a line arrangement including exactly two coaxial lines 12, 13, the inner conductors of which are each supplied with equally high voltages having opposite polarities.

Another embodiment relates to a line arrangement in which an isolation transformer with a center tap is provided on at least one end. In this the ends of a winding are connected to the inner conductors of the two coaxial lines, and the center tap of this winding is connected to the outer conductors or shields.

In another embodiment the outer conductors or shields of the at least two coaxial lines 12, 13 are connected to a circuit ground or a grounded conductor.

Another embodiment includes a cable having two inner conductors and a common outer conductor or shield, such as a Twinax cable.

Another embodiment relates to a coaxial cable in which the inner conductor is designed as an HF flexible or stranded wire. The outer conductor also can be designed to be an HF flexible or stranded wire, or a normal braided shield or a foil. An HF flexible or stranded wire is a flexible or stranded wire consisting of a multitude of wires which are all insulated from each other. Here it is of advantage to use enameled copper wires. With currents of medium frequencies an HF flexible or stranded wire has lower losses than a single wire or a flexible or stranded wire having wires which are not insulated from each other.

In another embodiment the coaxial cable has a further shield which can be grounded at one or both ends. The shield can be also designed as an HF flexible or stranded wire, or a normal braided shield, or a foil.

In another embodiment, the coaxial lines are divided along their lengths into at least two sections. At the transitions between the sections the two inner conductors are interconnected crosswise. Thus, forward and return conductors are interchanged.

To balance the capacitive leakage currents of both conductors with respect to the outer conductor or shield, at least one of the conductors can be separated by an additional capacitor from the potential of the outer conductor or shield.

Furthermore, all of the above-described embodiments or circuit variants which have been explained with reference to an inductive rotary joint can be also implemented using this general line arrangement. Moreover, the line arrangement can be used also in any other field of energy transmission.

In particular, any desired kind of balancing transformer such as a balun or also a guanella can be provided for the line arrangement as well as for the inductive rotary joint. A balancing transformer of this kind can be provided at one end of the line or at both ends of the line in order to balance the signal through the line, and thus to optimize the losses and also an undesired radiation of energy.

Further subject matter includes a computer tomograph having a rotary joint or line arrangement for power transmission as described herein. The line arrangement can be used also in a different place, for example for feeding the driving motor or the X-ray tube in computer tomographs.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. Inductive rotary joint, comprising:
    an inverter;
    an inductive rotary coupler having a primary winding and a secondary winding; in which the primary winding of the inductive rotary coupler is fed by the inverter via a first line, and energy transmitted by the inductive rotary coupler is delivered to a load from a secondary winding via a second line;
    wherein at least one of the first and second lines comprises at least two coaxial lines, each having an outer conductor and an inner conductor; the outer conductors are interconnected in an electrically conductive manner along a major part of their length; and
    each of the inner conductors is supplied by the inverter with voltages, with a sum of the voltages supplied to the inner conductors being substantially equal to zero.

2. Inductive rotary joint according to claim 1, wherein at least one of the lines comprises two coaxial lines; and each of the inner conductors of the two coaxial lines is supplied with equally high voltages of an opposite polarity.

3. Inductive rotary joint according to claim 1, wherein the inverter comprises a three-phase bridge circuit and generates a three-phase alternating signal.

4. Inductive rotary joint according to claim 2, wherein the inverter comprises a full bridge circuit and generates a balanced alternating signal.

5. Inductive rotary joint according to claim 2, wherein the inverter comprises a half-bridge circuit; and a transformer is connected between the inverter and the at least one line to generate a balanced alternating signal.

6. Inductive rotary joint according to claim 1, wherein an isolation transformer is connected between the inverter and the first line.

7. Inductive rotary joint according to claim 1, wherein the outer conductors of the at least two coaxial lines are interconnected in an electrically conducting manner along their entire length.

8. Inductive rotary joint according to claim 1, wherein the outer conductors of the at least two coaxial lines are interconnected in an electrically conductive manner via large surface-area contact.

9. Inductive rotary joint according to claim 1, wherein the outer conductors of the at least two coaxial lines are interconnected by a multitude of electrical connections.

10. Inductive rotary joint according to claim 1, wherein the outer conductors of the at least two coaxial lines are connected to at least one of a circuit ground and a grounded conductor.

11. Inductive rotary joint according to claim 1, wherein at least one coaxial line comprises an inner conductor with an HF flexible or stranded wire, and an outer conductor optionally with an HF flexible or stranded wire, a braided shield, or a foil.

12. Inductive rotary joint according to claim 1, wherein at least one coaxial line comprises an additional shield.

13. Inductive rotary joint according to claim 1, wherein at least one coaxial line is divided into at least two sections, with a forward line and a return line being interchanged in each case between the sections.

14. Inductive rotary joint according to claim 1, wherein at least one inner conductor of a coaxial line is electrically connected via a capacity to an outer conductor to balance leakage currents.

15. Inductive rotary joint, comprising
    an inverter;
    an inductive rotary coupler having a primary winding and a secondary winding, in which the primary winding of the inductive rotary coupler is fed by the inverter via a first line, and energy transmitted by the inductive rotary coupler is delivered to a load from a secondary winding via a second line;
    wherein the first and second lines each comprises at least one coaxial line having an inner conductor and an outer conductor, wherein the outer conductors of the first and second lines are interconnected in an electrically conductive manner along a major part of their length; and
    a sum of currents flowing through the inner conductor and the outer conductor is substantially equal to zero.

16. Inductive rotary joint according to claim 15, wherein at least one coaxial line comprises an inner conductor with an HF flexible or stranded wire, and an outer conductor optionally with an HF flexible or stranded wire, a braided shield, or a foil.

17. Inductive rotary joint according to claim 15, wherein at least one coaxial line comprises an additional shield.

18. Inductive rotary joint according to claim 15, wherein at least one coaxial line is divided into at least two sections, with a forward line and a return line being interchanged in each case between the sections.

19. Inductive rotary joint according to claim 15, wherein at least one inner conductor of a coaxial line is electrically connected via a capacity to an outer conductor to balance leakage currents.

20. Line arrangement for coupling-on a load to an inverter, comprising at least two coaxial lines, each having an outer conductor and an inner conductor, wherein the outer conductors of the at least two coaxial lines are interconnected in an electrically conductive manner along a major portion of their length; and each of the inner conductors is supplied with voltages, with a total sum of the voltages supplied to the inner conductors being substantially equal to zero.

21. Line arrangement according to claim 20, wherein the inner conductors of the two coaxial lines are supplied with equally high voltages of opposite polarity.

22. Line arrangement according to claim 21, wherein an isolation transformer with a central tap and two winding ends is provided on at least one end of the line arrangement; and
   each winding end is connected to a respective inner conductor of the two coaxial lines, and the center tap is connected to the outer conductors.

23. Line arrangement according to claim 20, wherein the outer conductors of the at least two coaxial lines are connected to at least one of a circuit ground and a grounded conductor.

24. Computer tomograph comprising an inductive rotary joint according to claim 1.

25. Computer tomograph comprising an inductive rotary joint according to claim 15.

26. Computer tomograph comprising a line arrangement according to claim 20.

* * * * *